(12) United States Patent
Batchelor et al.

(10) Patent No.: US 9,918,774 B2
(45) Date of Patent: Mar. 20, 2018

(54) RESISTIVELY HEATED ELECTROSURGICAL DEVICE

(71) Applicant: GYRUS ACMI, INC., Southborough, MA (US)

(72) Inventors: Kester J. Batchelor, Mound, MN (US); Richard J. Curtis, Maple Grove, MN (US); John Mensch, Plymouth, MN (US); Jyue Boon Lim, New Brighton, MN (US); Riyad Moe, Madison, WI (US)

(73) Assignee: GYRUS ACMI, INC., Southborough, MA (US)

( * ) Notice: Subject to any disclaimer, the term of this patent is extended or adjusted under 35 U.S.C. 154(b) by 405 days.

(21) Appl. No.: 14/708,836

(22) Filed: May 11, 2015

(65) Prior Publication Data

US 2015/0320485 A1    Nov. 12, 2015

Related U.S. Application Data

(60) Provisional application No. 61/991,644, filed on May 12, 2014.

(51) Int. Cl.
*A61B 18/14* (2006.01)
*A61B 18/08* (2006.01)
(Continued)

(52) U.S. Cl.
CPC .............. *A61B 18/08* (2013.01); *A61B 18/04* (2013.01); *A61B 18/082* (2013.01);
(Continued)

(58) Field of Classification Search
None
See application file for complete search history.

(56) References Cited

U.S. PATENT DOCUMENTS 4,196,734 A    4/1980  Harris
4,493,320 A    1/1985  Treat
(Continued)

FOREIGN PATENT DOCUMENTS

DE    3215055 A1    10/1983
EP    1878399 A1    1/2008
(Continued)

OTHER PUBLICATIONS

Written Opinion of the International Preliminary Examining Authority for International Application No. PCT/US2015/030135, dated Sep. 8, 2016.
(Continued)

*Primary Examiner* — Brian T Gedeon
(74) *Attorney, Agent, or Firm* — The Dobrusin Law Firm P.C.

(57) ABSTRACT

A medical device is provided that includes a hand piece, a heating power supply, and a therapy power supply. The hand piece includes a first electrode including a heater. The heating power supply selectively provides heating power to the heater. The therapy power supply selectively provides therapeutic power to the first electrode. The medical device is changeable between operating a first electrosurgical configuration and a second electrosurgical configuration. In the first electrosurgical configuration, the heating power supply provides the heating power to the heater to heat the first electrode and the therapy power supply provides the therapeutic power to the first electrode.

27 Claims, 8 Drawing Sheets

(51) Int. Cl.
    *A61B 18/16*           (2006.01)
    *A61B 18/04*           (2006.01)
    *A61B 18/00*           (2006.01)

(52) U.S. Cl.
    CPC ............ *A61B 18/085* (2013.01); *A61B 18/14* (2013.01); *A61B 18/1442* (2013.01); *A61B 18/1445* (2013.01); *A61B 18/16* (2013.01); *A61B 2018/00589* (2013.01); *A61B 2018/00601* (2013.01); *A61B 2018/00607* (2013.01); *A61B 2018/00916* (2013.01); *A61B 2018/00958* (2013.01); *A61B 2018/00994* (2013.01); *A61B 2018/1412* (2013.01); *A61B 2018/1417* (2013.01); *A61B 2018/1422* (2013.01); *A61B 2018/1452* (2013.01); *A61B 2018/1455* (2013.01); *A61B 2018/1462* (2013.01); *A61B 2018/1467* (2013.01)

(56) References Cited

U.S. PATENT DOCUMENTS

| | | | |
|---|---|---|---|
| 4,905,691 A | 3/1990 | Rydell | |
| 5,250,046 A | 10/1993 | Lee | |
| 5,807,392 A | 9/1998 | Eggers | |
| 6,221,039 B1 | 4/2001 | Durgin et al. | |
| 6,235,027 B1 | 5/2001 | Herzon | |
| 6,471,701 B2 | 10/2002 | Brommersma | |
| 6,533,778 B2 | 3/2003 | Herzon | |
| 6,610,056 B2 | 8/2003 | Durgin | |
| 6,827,717 B2 | 12/2004 | Brommersma | |
| 7,211,079 B2 | 5/2007 | Treat | |
| 7,276,068 B2 | 10/2007 | Johnson et al. | |
| 7,326,202 B2 | 2/2008 | McGraffigan | |
| 7,922,713 B2 | 4/2011 | Geisel | |
| 8,382,748 B2 | 2/2013 | Geisel | |
| 8,430,870 B2 | 4/2013 | Manwaring et al. | |
| 8,435,237 B2 | 5/2013 | Bahney | |
| 8,491,578 B2 | 7/2013 | Manwaring et al. | |
| 2003/0040744 A1 | 2/2003 | Latterell et al. | |
| 2003/0130658 A1 | 7/2003 | Goble et al. | |
| 2007/0156137 A1 | 7/2007 | Geisel | |
| 2008/0015575 A1 | 1/2008 | Odom et al. | |
| 2009/0248002 A1 | 10/2009 | Takashino et al. | |
| 2010/0268211 A1 | 10/2010 | Manwaring et al. | |
| 2010/0331621 A1 | 12/2010 | St. George et al. | |
| 2011/0077629 A1 | 3/2011 | Tanaka et al. | |
| 2012/0296325 A1 | 11/2012 | Takashino | |
| 2014/0276786 A1 | 9/2014 | Batchelor | |
| 2014/0276795 A1 | 9/2014 | Batchelor et al. | |
| 2014/0276796 A1 | 9/2014 | Batchelor et al. | |
| 2014/0276797 A1 | 9/2014 | Batchelor et al. | |
| 2014/0276804 A1 | 9/2014 | Batchelor | |
| 2015/0032094 A1 | 1/2015 | Kane et al. | |

FOREIGN PATENT DOCUMENTS

| | | |
|---|---|---|
| EP | 2491880 A1 | 8/2012 |
| EP | 2848224 A2 | 3/2015 |
| JP | 2008-023335 A | 2/2008 |
| JP | 2009-247893 A | 10/2009 |
| WO | 2011/064881 A1 | 4/2013 |
| WO | 2013/103934 A1 | 7/2013 |

OTHER PUBLICATIONS

International Preliminary Report on Patentability for International Application No. PCT/US2015/030135, dated Oct. 27, 2016.
International Search Report and Written Opinion for International Application No. PCT/US2015/030135, dated Nov. 6, 2015.
Japanese Office Acton for Japanese Application No. 2016-567389, dated Sep. 5, 2017.

RESISTIVELY HEATED ELECTROSURGICAL DEVICE

This application claims priority to U.S. Provisional Patent Application No. 61/991,644 filed on May 12, 2014, the contents of which is incorporated by reference herein in its entirety for all purposes.

FIELD

The present teachings relate to a medical device, and more specifically to an electrosurgical medical device that combines thermal, therapeutical, and mechanical modalities.

BACKGROUND

Electrosurgical medical devices generally fall into one of two categories: monopolar medical devices and bipolar medical devices. A monopolar medical device includes an active electrode electrically connected to an electrosurgical generator. A return electrode, typically in the form of a patient pad, is also electrically connected to the electrosurgical generator and can be placed in contact with a patient. In use, electrical current is passed from the electrosurgical generator to the active electrode, through a site or a region of the patient's anatomy (i.e., a tissue or a vessel) to the patient pad, and back to the electrosurgical generator.

A bipolar medical device includes an active electrode and a return electrode adjacent the active electrode, both of which are electrically connected to an electrosurgical generator. In use, a site or a region of the anatomy is placed between the active and return electrodes, and electrical current passes from the electrosurgical generator to the active electrode, through the site or a region of the anatomy to the adjacent return electrode, and then back to the electrosurgical generator.

Examples of electrosurgical medical devices may be found in U.S. Pat. Nos. 4,196,734; 5,807,392; 7,211,079; 7,276,068; 7,922,713; 8,382,748; 8,491,578 and U.S. Patent Application Publication No. 2010/0331621 all of which are incorporated by reference herein in their entirety for all purposes.

While both monopolar and bipolar medical devices are desirable for use in various medical procedures, both have inherent shortcomings, however. For example, monopolar medical devices are known to pass relatively high electrical currents through the patient, which may cause unwanted tissue and/or organ damage. Moreover, some procedures cannot allow the use of monopolar medical devices because of high thermal spread and dispersed energy format. While bipolar medical devices minimize these shortcomings, accurately controlling which electrode is the active electrode is difficult.

It would therefore be desirable to have a medical device that can address at least one of the aforementioned shortcomings. For example, it would be attractive to have a single electrosurgical medical device that can be used in both monopolar and bipolar modes. It would be desirable to have an electrosurgical medical device that can be quickly switch between a monopolar mode and a bipolar mode. It would be advantageous to have medical device that can be used in a variety of arrangements in each mode. It would be attractive to have an electrosurgical medical device that uses less power and voltage, and therefore less current to perform a device function. It would be attractive to have an electrosurgical medical device with a plurality of electrodes, in which one or more of the electrodes are resistively heated to allow for thermionic disassociation of the electrons, ions, or both so that electrons, ions, or both in a field are accelerated. In this regard, it would be desirable because less voltage may be required to get the same disassociation of the electrons, ions, or both than with only voltage.

SUMMARY

The present teachings provide a medical device that addresses at least one of the aforementioned shortcomings. For example, the teachings herein provide a single electrosurgical medical device that can be used in both monopolar and bipolar modes. The teachings herein also provide an electrosurgical medical device that can be quickly switch between a monopolar mode and a bipolar mode. The electrosurgical medical device according to the present teachings provide a device that uses less power and voltage, and therefore less current to perform a device function. In each mode, the medical device according to the teachings herein can be used in a variety of arrangements. The teachings herein provide an electrosurgical medical device with a plurality of electrodes, in which one or more of the electrodes are resistively heated to allow for thermionic disassociation of the electrons, ions, or both so that electrons, ions, or both in a field are accelerated. In this regard, the present teachings require less voltage to get the same disassociation of the electrons, ions, or both than with only voltage.

The present teachings provide a medical device that includes a hand piece, a heating power supply, and a therapy power supply. The hand piece includes a first electrode including a heater. The heating power supply selectively provides heating power to the heater. The therapy power supply selectively provides therapeutic power to the first electrode. The medical device is changeable between operating a first electrosurgical configuration and a second electrosurgical configuration. In the first electrosurgical configuration, the heating power supply provides the heating power to the heater to heat the first electrode and the therapy power supply provides the therapeutic power to the first electrode.

The present teachings also provide a medical device, comprising a hand piece, a heating power supply, and a therapy power supply. The hand piece comprises a first electrode including a heater, a second electrode, and a third electrode. The heating power supply selectively supplies heating power to the heater. The therapy power supply selectively provides therapeutic power to the first, second, and/or third electrodes. The medical device is selectively changeable between a first electrosurgical configuration and a second electrosurgical configuration. In the first electrosurgical configuration, the heating power supply provides the heating power the heater to heat the first electrode and the therapy power supply provides the therapeutic power to the first electrode.

DETAILED DESCRIPTION

Figure 1:
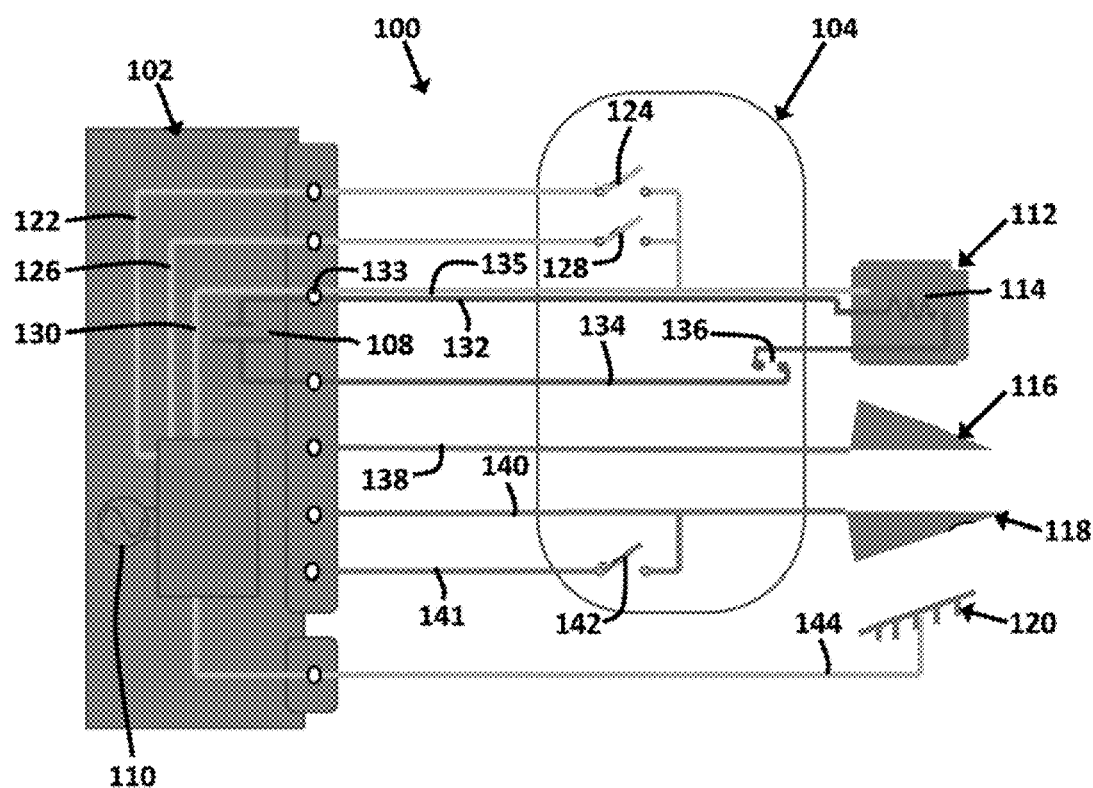
FIG. 1 illustrates a schematic circuit of a medical device according to the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a medical device. More specifically, the present teachings relate to a medical device and associated componentry of an electrosurgical medical device. The teachings herein can be applied to any medical device. For example, some non-limiting and exemplary electrosurgical medical devices include forceps, scissors, scalpels, spatulas, J-hooks, graspers, snares, resectoscopes, tweezers, the like, or a combination thereof. The one or more electrosurgical medical devices can be used in one or more arrangements, configurations or modes (i.e., monopolar, bipolar, or both). The electrosurgical medical device may combine one or more thermal, electrosurgical, and mechanical modalities. The electrosurgical medical device may be used in electrosurgery. The electrosurgical medical device can be used in any medical procedure to perform any device function. For example, the medical procedure may be any invasive procedure, minimally invasive procedure, or both. Some non-limiting device functions may include effecting hemostasis; coagulating blood; grasping, manipulating, cutting, transecting, sealing, cauterizing, desiccating, ablating, welding, fulgurating, vaporizing, and/or otherwise effecting an object or any area of the anatomy such as tissue or a vessel.

The electrosurgical medical device can be selectively switched between at least two electrosurgical operating configurations. That is, the electrosurgical medical device can be switched between a first electrosurgical operating configuration and a second electrosurgical operating configuration. In each electrosurgical operating configuration, the electrosurgical medical device can be used in a variety of arrangements and modes. For example, in each operating arrangement or configuration, the electrosurgical medical device can be used in one or more monopolar modes and one or more bipolar modes. The electrosurgical medical device of the present teachings can be easily switched between the various operating arrangements, configurations and modes. More specifically, a surgeon can switch between operating arrangements, configurations and modes before or during a medical procedure without changing devices, without needing a second hand, without disrupting and/or prolonging the medical procedure, or a combination thereof. Such "switchable" electrosurgical medical devices may include an electrosurgical blade, or they may include other features, which may form a medical device that does not include a blade. For example, such "switchable" medical devices may be a forceps, tweezers, segments of a medical spatula or J-hook, a snare, resectoscope, etc. The electrosurgical medical device may also operate in a single mode; that is, the electrosurgical device may not be switchable between at least two electrosurgical operating conditions like in the aforementioned examples. Such "non-switchable" electrosurgical medical devices may include an electrosurgical blade, or they may include other features, which may form a medical device that does not include a blade. For example, such medical devices may be a forceps, tweezers, segments of a medical spatula or J-hook, a snare, resectoscope, etc.

The electrosurgical medical device may include a hand piece. The hand piece may function to provide a gripping or grasping area for handling the electrosurgical medical device. The hand piece may include one or more controls for operating the electrosurgical medical device. For example, the one or more controls may function to control, move, extend, retract, and/or manipulate one or more functional features and/or the one or more extensions to perform a device function during a medical procedure. The one or more controls may also control communication of power and/or signals between the one or more generators and the electrosurgical medical device. That is, in use, the one or more controls may control the type and/or the amount of power, the type and/or amount of signals, or both that are communicated between the one or more generators and the electrosurgical medical device. In other words, the one or more controls may control whether monopolar or bipolar power is communicated between the one or more generators to the electrosurgical medical device; whether heating power, RF power, or both is communicated between the one or more generators to the electrosurgical medical device; and/or which of the one or more electrodes the power and/or signals are communicated to. Moreover, the one or more controls may control the particular operating arrangement, configuration and/or mode in which the electrosurgical medical device is used. The one or more controls may include one or more knobs, switches, slides, buttons, etc. The hand piece may include one or more connections (i.e., plugs, ports, chords, etc.) for connecting the electrosurgical medical device to one or more generators, to one or more auxiliary devices, or both.

The electrosurgical medical device may include one or more extensions. The one or more extensions may be used to perform a device function in any medical procedure. For example, the one or more extensions may assist effecting hemostasis; coagulating blood; grasping, manipulating, cutting, transecting, sealing, cauterizing, desiccating, ablating, welding, fulgurating, vaporizing, and/or otherwise effecting an object or any area of the anatomy such as tissue or a vessel. The one or more extensions may grip, hold, squeeze, manipulate, handle, and/or move any object. The electrosurgical medical device may comprise any number of extensions. For example, the electrosurgical medical device may comprise one or more extensions, two or more extensions, preferably three or more extensions, or even four or more extensions. The electrosurgical medical device may have preferably three of less extensions, two or less extensions, or even one extension.

The one or more extensions may be moveable or immoveable. For example, one or more extensions may be moveable, while one or more extensions may be immobilized. The one or more extensions may be moved or otherwise manipulated via one or more controls on the hand piece, one or more controls at a remote location (i.e., a foot pedal, a remote computer, etc.), or both. The one or more extensions may be moved in any way or direction to perform a device function. For example, one or more extensions may be advanced, extended, retracted, opened, closed, pivoted, rotated, articulated, actuated, reciprocated, clamped, the like, or a combination thereof. The one or more extensions may be axially moved, longitudinally moved, moved along an arc, or a combination thereof. The one or more extensions may be moved individually, together in unison, sequentially, or a combination thereof. The one or more extensions may be moveable or immovable so that the electrosurgical medical device can be used as any medical device to perform a device function. The one or more extensions may form one or more portions or segments of an arm, jaw, blade, scalpel, or portions of any medical device, such as a snare, forceps, scissors, scalpels, spatulas, J-hooks, graspers, resectoscopes, tweezers, the like, the combination of. One extension may be a center extension, which may be adjacent or sandwiched between two outer extensions (i.e., arranged as a spatula, J-hook, etc.) The one or more extensions may function as a blade, a blade electrode, or both. The one or more blades, blade electrodes, or both may be advanced beyond a distal end of one or more extensions to cut or transect a part of the anatomy, such as a vessel or tissue. The one or more blades, blade electrodes, or both may be advanced beyond a distal end of the one or more extensions to cauterize a vessel or tissue or coagulate blood. One or more extensions may move or pivot so that that a vessel, tissue, or object can be gripped, grasped, squeezed, manipulated, sealed, held, moved, and/or other wise gripped.

The one or more extensions may comprise or be fabricated from any material. Preferably, the one or more extensions are fabricated from any material that is safe for use in an electrosurgical procedure. For example, the one or more extensions may be fabricated from one or more metals, plastics, polymers, elastomers, gold, silver, copper, titanium, aluminum, iron based metals, stainless steel, silicone, polytetrafluoroethylene (PTFE), insulating polymers, rubber, or a combination thereof.

The one or more extensions may include one or more functional features that may assist in performing a device function. Exemplary and non-limiting functional features may include one or more or various teeth, serrations, mouse teeth, smooth portions, sharp edges, cutouts, notches, wires, scalpels; features or segments of a J-hook; features or segments of a Spatula; features or segments of a snare; features or segments of a forceps; features or segments of a resectoscope; the like, or a combination thereof.

The one or more functional features, extensions, or portions of the one or more functional features or extensions, or a combination thereof, may comprise one or more active portions. The one or more active portions may function to contact a portion of the anatomy to perform a device function thereon or thereto. In other words, the one or more active portions may be in communication with the one or more generators, the one or more electrodes, the one or more extensions, the one or more functional features, or a combination thereof and may function to transmit power, signals, or both to or through the anatomy. The one or more functional features, extensions, or both may include one or more insulating portions. The one or more insulating portions may prevent accidental or inadvertent arching or shorting between adjacent active portions, electrodes, or both. Preferably, each extension, functional feature, or a combination thereof is coated with an insulating material. The one or more extensions may be coated with an insulating material in regions where a user contacts the one or more extensions. The one or more insulating portions may comprise any insulating material. For example, the one or more insulating portions may be such silicone or polytetrafluoroethylene.

The electrosurgical medical device may include one or more electrodes. In use, electrical current, power, and/or signals can be communicated between the one or more generators and the one or more electrodes so that a device function can be performed on a site or region of the anatomy with the one or more extensions, functional features, active portions, or a combination thereof. The one or more electrodes may be any conducting instrument, device, or probe. The one or more electrodes may be a loop electrode. The one or more electrodes, loop electrodes, or both may be a monopolar, bipolar, or both. The one or more electrodes may be fabricated from any material that is safe for use in electrosurgery and suitable for performing one or more device functions. The one or more electrodes with a heater may be fabricated from any material, such as Nichrome. The one or more electrodes may be in electrical communication with the one or more generators. The one or more electrodes may be in electrical communication with the one or more generators via one or more connections, which may be one or more wires. The one or more electrodes may be in communication with the one or more extensions, active portions, functional features, or a combination thereof. One electrode may be in communication with one extension. Alternatively, more than one electrode can be in communication with a single extension. One or more insulating materials may surround the one or more electrodes to prevent accidental and/or inadvertent arching therebetween.

One or more of the electrodes may include a heater. The heater may be any feature, material, or device that may heat the one or more electrodes. The heater may be provided with electrical power, heating power, therapeutic power, one or more signals, or a combination thereof from any source to resistively heat the one or more electrodes. Preferably, the heater receives heating power from the one or more generators to heat the one or more electrodes with the heater. More preferably, the heater receives heating power from the heating power source. The heater may be, for example, a resistor, a wire, a ferromagnetic material, the like, or a combination thereof. The heating power may be constantly supplied to the heater, or the heating power may be selectively supplied to the heater to heat the one or more electrodes. The heating power can be supplied to the heater at any time. In other words, the heating power can be supplied to the heater before therapeutic power is supplied to the electrode, while therapeutic power is being supplied to the electrode, or after therapeutic power has been supplied to the electrode. The heating power can be supplied to the heater to heat the one or more electrodes before or while performing a device function. The heating power can be supplied to the heater via a constant signal, or the heating power can be pulsed, oscillated, or both. The heating power can be supplied to the heater on an "as-needed" basis to maintain the one or more heaters/electrodes at a predetermined and desired temperature; to elevate the one or more heaters/electrodes to a predetermined temperature; to allow the temperature of the one or more electrodes to drop, or a combination thereof, for example. The heating power may be controlled via the hand piece, one or more controls on the hand piece, one or more controls at a remote location (i.e., a foot pedal, a remote computer, etc.), or a combination thereof. The heater may function to provide thermal cutting.

A resistively heated electrode may allow for thermionic disassociation of the electrons, ions, or both. That is, by resistively heating the one or more of the electrodes, electrons, ions, or both in an electrical field are accelerated. Thermionic disassociation may be advantageous because less voltage may be required to get the same disassociation of the electrons, ions, or both than with only voltage. In other words, a greater total energy is possible with lower voltage. Moreover, in a bipolar mode, a heated electrode is more likely to activate as an intended source of therapeutic current (i.e., the active electrode) providing the surgeon with greater control of the location of the intended tissue effect. The one or more electrodes with a heater may be heated even if the one or more electrodes with a heater are not specifically configured or arranged to perform a device function. For example, if one or more other electrode/extension combinations are used to perform a device function (i.e., a second and third extension), the one or more electrodes with a heater (i.e., a first extension) may nonetheless still be heated. Alternatively, the one or more electrodes with a heater may be restricted from being heated in an arrangement or configuration where they are not used to perform a device function. Again, this may be controlled via the hand piece, one or more controls on the hand piece, one or more controls at a remote location (i.e., a foot pedal, a remote computer), or a combination thereof.

The electrosurgical medical device may include, or be in communication with, one or more generators. The one or more generators may function to provide power, signals, or both to the electrosurgical medical device. The one or more generators may function to provide power, signals, or both to the electrosurgical medical device so that the electrosurgical medical device can perform a device function. The device function(s) may include, but are not limited to, any of the examples recited above. The one or more generators may be powered by any energy source or power source. For example, the one or more generators may be powered by AC power, DC power, or a combination of AC and DC power.

The one or more generators may provide any power and/or any signal to the electrosurgical medical device. For example, the power or signal may be a therapeutic power, a heating power, an RF power, a monopolar power or signal, a bipolar power or signal, an electric signal, an electric current, a voltage, an oscillating electrical energy, or a combination thereof. Preferably, both therapeutic power and heating power is provided by the one or more generators. The one or more generators may include a heating power supply, a therapy power supply, or both. The heating power supply may supply heating power, therapeutic power, or both to the electrosurgical medical device. The therapy power supply may supply therapeutic power, heating power, or both to the electrosurgical medical device. The heating power may be the same as the therapeutic power, or may be different. The heating power may be any electrical signal that is communicated to a heater associated with one or more of the electrodes. The heating power may heat the heater and therefore resistive heat the one or more electrodes. The heating power may be an electrical current or signal that remains within the circuit and is restricted or prevented from transferring to a portion of the anatomy. The therapeutic power may be an electrical current or signal that is communicated or transmitted to or through the anatomy to perform a device function thereon. The therapeutic power may be a monopolar signal, a bipolar signal, or both. The monopolar signal may be any signal that has a voltage differential between an active port and a return port on the generator. The monopolar signal may be any signal that when applied by the electrosurgical medical device extends from one pole of an electrode or extension to another pole located at a remote location (i.e., to the patient pad). The monopolar signal may be selectively applied by opening or closing one or more switches or controls on the hand piece; one or more switches or controls extending between the one or more generators and the one or more electrodes (i.e., a foot pad), one or more controls or switches at a remote location (i.e., a remote computer), or a combination thereof. The bipolar signal may be any signal that has a voltage differential between two electrodes connected to the electrosurgical medical device.

The one or more generators may include one or more connections. The one or more connections may be any connection, port, plug, inlet, outlet, etc. for supplying, transmitting, or communicating the power, signals, or both between the one or more generators and the electrosurgical medical device. For example, the one or more connectors may include one or more active ports and one or more return ports that may cooperate to form a closed circuit. The one or more generators may include one or more controls (i.e., switches, buttons, knobs, foot pedals, etc.) so that power, signals, or both can be selectively supplied to the electrosurgical device based on a desired operating mode, arrangement, and/or configuration, for example. The one or more generators may include a central processing unit (CPU), a series of internal switching, or both. The internal switching may provide a signal from an activation circuit to the voltage source so that the voltage source can be supplied to the electrosurgical medical device. The CPU may be interchanged with the internal switching and the switching may perform the same functions as the CPU. The CPU may be any device that supplies power, current, electrical reconfiguration; may be a switch between two or more powers (i.e., heating power, therapeutic power, or both); a switch between two or more arrangements, modes or configurations, or a combination thereof. The CPU may be used to switch the electrosurgical medical device between one or more modes, arrangements, configurations, or a combination thereof.

One or more remote electrodes may be in electrical communication with the one or more generators, the electrosurgical medical device, or both. The one or more remote electrodes may be one or more patient pads. The one or more remote electrodes or patient pads may complete a circuit for the transfer or communication of power, signals, or both between the one or more generators and at least one of the electrodes. The one or more patient pads may be used in a monopolar operating mode. For example, in use, one or more therapeutic signals from the one or more generators may be provided to one or more electrodes, through the anatomy of the patient, and back to the one or more generators via the one or more patient pads. In use, the one or more patient pads may be placed in at a remote location. For example, the one or more patient pads may be placed in physical contact, electrical contact, or both with a patient. In other words, depending on the type of medical procedure, the one or more patient pads may be in contact with a patient lying or sitting on the one or more patient pads; in contact with a patient's back; on or around an arm or leg of a patent; in contact with a patient chest; etc.

FIG. 1 illustrates a schematic circuit of an electrosurgical medical device 100. The electrosurgical medical device 100 includes a generator 102 and a hand piece 104. The generator 102 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114. A remote or patient pad 120 is in electrical communication with the electrosurgical medical device 100 and the therapy power supply 110.

A first therapeutic power connection 122, which includes a first therapeutic power switch 124, extends between the therapy power supply 110 and the first electrode 112. A second therapeutic power connection 126, which includes a second therapeutic power switch 128, extends between the therapy power supply 110 and the first electrode 112. A third therapeutic power connection 130 extends between the therapy power supply 110 and the first electrode 112, which provides therapeutic power to the first electrode 112. When the first therapeutic power switch 122, the second therapeutic power switch 128, or both is open, therapeutic power is restricted from communicating to the first electrode 112. However, when at least one of the first and second therapeutic power switches 124, 128 are closed, therapeutic power is provided from the therapy power supply 110 to the first electrode 112.

A first heating power connection 132 extends between the heating power supply 108 and the heater 114 of the first electrode 112. The first heating power connection 132 and the third therapeutic power connection 130 can be electrically connected 133 or a single, common connection 135 carrying two signals from the generator 102. That is, the connection 135 can carry therapeutic power to the first electrode 112 and heating power to the heater 114. A second heating power connection 134, which includes a heating power switch 136, extends between the heating power supply 108 and the first electrode 112. When the heating power switch 136 is closed, heating power is provided from the heating power source 108 to the heater 114 to heat the first electrode 112. When the heating power switch 136 is open, heating power is restricted from communicating to the heater 114 and, as such, the first electrode 112 is not heated.

A fourth therapeutic power connection 138 and a fifth therapeutic power connection 140 extends between the therapy power supply 110 and a corresponding second and third electrode 116, 118. A sixth therapeutic power connection 141, which includes an electrode switch 142, extends between the therapy power supply 110 and third electrode 118. A patient pad connection 144 extends between the therapy power supply 110 and the remote or patient pad 120.

When at least one of the first and second therapeutic power switches 124, 128 are closed, therapeutic power can be communicated from the therapy power supply 110 to the first electrode 112 and communicated back to the therapy power supply 110 via the second electrode 116, the third electrode 118, or both (i.e., bipolar mode). Alternatively, the therapeutic power can be communicated back to the therapy power supply 110 via the patient pad 120 (monopolar mode).

Moreover, by closing the electrode switch 142, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the heating power switch 136 can be opened to prevent the supply of heating power to the heater 114 while therapeutic power is being communicated between the second and third electrodes 116, 118. Moreover, one of the therapeutic power switches 124, 128 can be opened to prevent the supply of therapeutic power to the first electrode 112 while therapeutic power is being communicated between the second and third electrodes 116, 118.

Figure 2A:
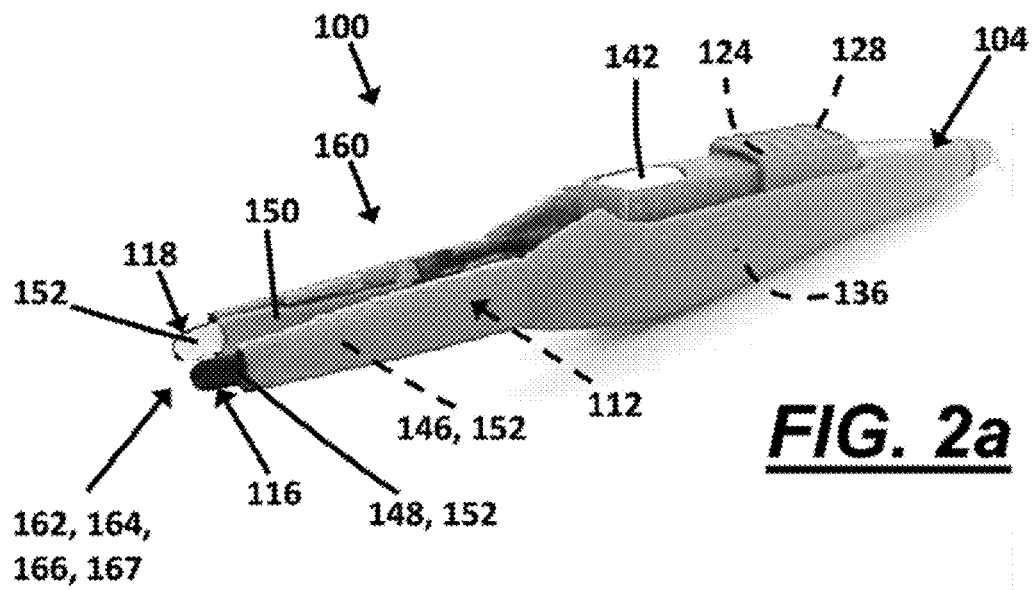
FIG. 2a illustrates a perspective view of a medical device according to the teachings herein.

FIG. 2a illustrates an exemplary electrosurgical medical device 100 in a bipolar operating mode 160. The electrosurgical medical device 100 includes a hand piece 104, a first extension 146, a second extension 148, and a third extension 150. The extensions 146, 148, 150 include at least one function feature 152. The first electrode 112 is in communication with the first extension 146, the second electrode 116 is in communication with the second extension 148, and the third electrode 118 is in communication with the third extension 150. The first extension 146 is longitudinally moveable relative to both the second and third extensions 148, 150. That is, the first extension 146 can be independently moved and extended beyond the second extension 148 and the third extension 150, and can be retracted therebetween. To perform a device function in the bipolar operating mode 160, the electrosurgical medical device 100, and more specifically, the electrodes and the extensions can be used in a variety of arrangements, such as a first arrangement 162, a second arrangement 164, a third arrangement 166, and a fourth arrangement 167.

With reference to FIGS. 1 and 2a, in the first arrangement 162, therapeutic power is provided to the second and third electrodes 116, 118. More specifically, therapeutic power is provided from the therapy power supply 110 to the second electrode 116 via the fourth therapeutic power connection 138. The electrode switch 142 is closed and therapeutic power is provided from the therapy power supply 110 to the third electrode 118. Accordingly, therapeutic power can flow between the second and third electrodes 116, 118. In use, a selected portion of the anatomy can be placed between the second and third extensions 148, 150 and in contact with the functional features 152 of one or both of the extensions 148, 150. Thus, a device function can be performed on that portion of the anatomy using the second and third electrodes 116, 118.

In the second arrangement 164, therapeutic power is provided to the first and second electrodes 112, 116. More specifically, therapeutic power is provided from the therapy power supply 110 to the first electrode 112 via the third therapeutic power connection 130, and to the second electrode 116 via the fourth therapeutic power connection 138. Accordingly, therapeutic power flows between the first and second electrodes 112, 116. In use, a selected portion of the anatomy can be placed between the first and second extensions 146, 148, and in contact with at least one of the functional features 152 thereof. Thus, a device function can be performed using the first and second electrodes 112, 116. While performing a device function in the second bipolar configuration 164, the first electrode 112 can be optionally heated. That is, by closing the heating power switch 136 and supplying heating power from the heating power supply 108 to the heater 114, the first electrode 112 can be resistively heated. Moreover, by closing one or both of the switches 124, 128, therapeutic power can be provided from the therapy power supply 110 to the first electrode 112 and back to the therapy power supply 110 via the remote or patient pad 120 (not illustrated).

Figure 4:
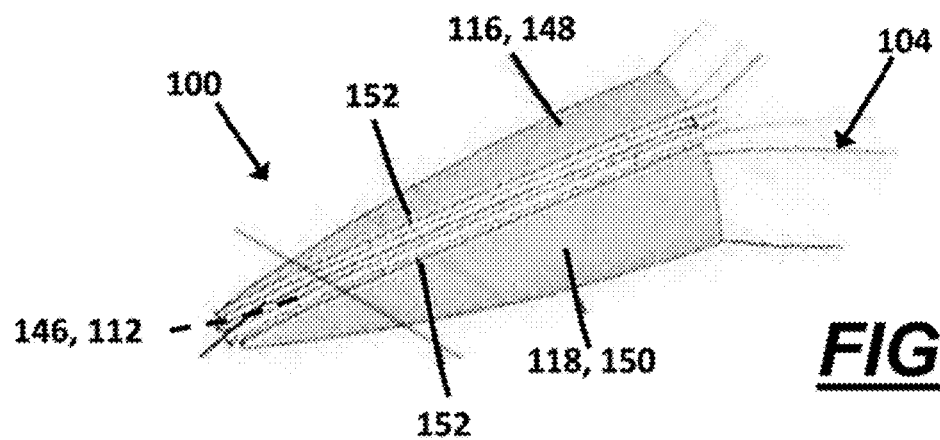
FIG. 4 illustrates a perspective view of a medical device according to the teachings herein.
Figure 5:
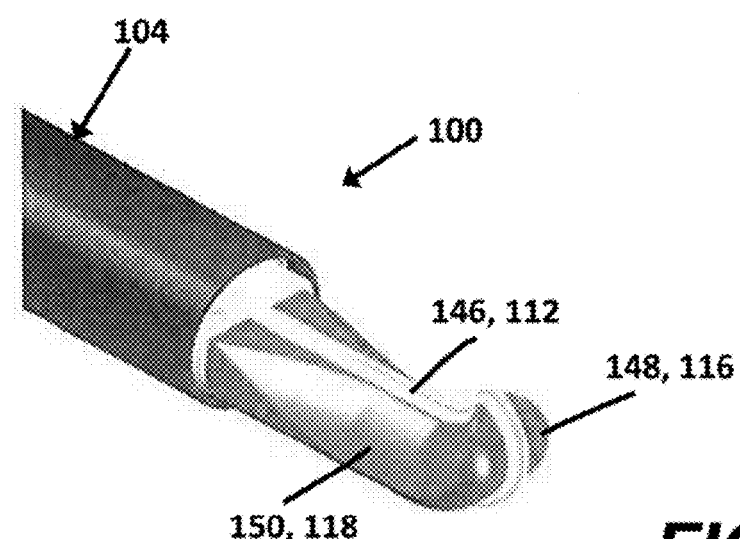
FIG. 5 illustrates a perspective view of a medical device according to the teachings herein.
Figure 6:
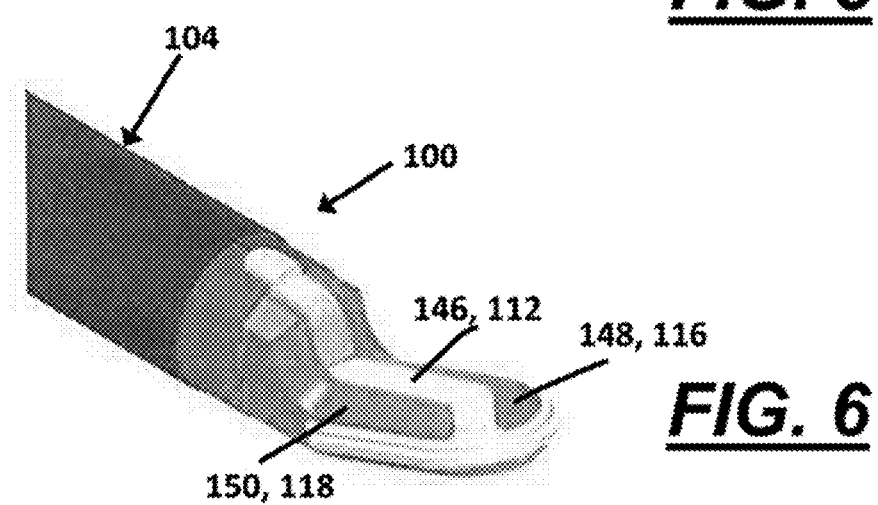
FIG. 6 illustrates a perspective view of a medical device according to the teachings herein.

In the third arrangement 166, which may be also relevant to the electrosurgical medical devices 100 shown in FIGS. 4-6, therapeutic power is provided to the first and third electrodes 112, 118. More specifically, therapeutic power is provided from the therapy power supply 110 to the first electrode 112 via the third therapeutic power connection 130. The electrode switch 142 is closed and therapeutic power is provided from the therapy power supply 110 to the third electrode 118. Accordingly, therapeutic power flows between the first and third electrodes 112, 118. In use, a selected portion of the anatomy can be placed between the first and third extensions 146, 150, and in contact with at least one of the functional features 152 thereof. Thus, a device function can be performed using the first and third electrodes 112, 118. While performing a device function in this arrangement, the first electrode 112 can be optionally heated. That is, by closing the heating power switch 136 and supplying heating power from the heating power supply 108 to the heater 114, the first electrode 112 can be resistively heated. Moreover, by closing one or both of the switches 124, 128, therapeutic power can be provided from the therapy power supply 110 to the first electrode 112 and back to the therapy power supply 110 via the remote or patient pad 120 (not illustrated).

In the fourth arrangement 167, therapeutic power is communicated between to the first electrode and both the second and third electrodes 116, 118. More specifically, therapeutic power is provided from the therapy power supply 110 to the first electrode 112 via the third therapeutic power connection 130. The electrode switch 142 is closed and at least a portion of the therapeutic power can be provided from the first electrode 112 to the third electrode 118 and back to the therapy power supply 110. Additionally, at least another portion of the therapeutic power can be provided from the first electrode 112 to the second electrode 116 and back to the therapy power supply 110. While performing a device function in the fourth bipolar configuration 167, the first electrode 112 can be optionally heated. That is, by closing the heating power switch 136 and supplying heating power from the heating power supply 108 to the heater 114, the first electrode 112 can be resistively heated.

Figure 2B:
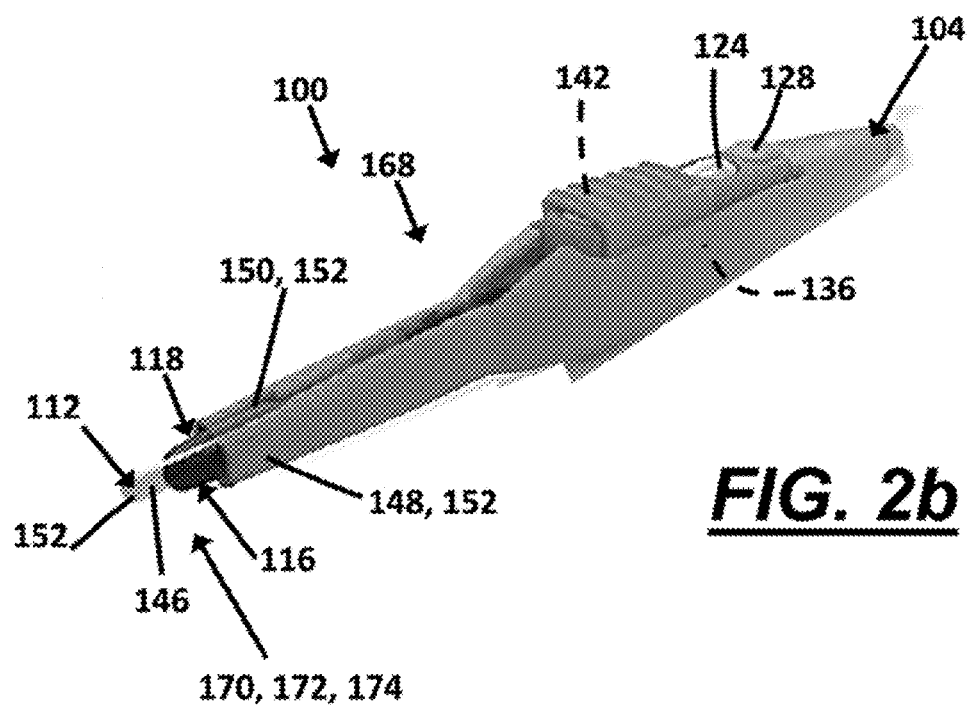
FIG. 2b illustrates a perspective view of a medical device according to the teachings herein.

FIG. 2b illustrates an electrosurgical medical device 100 in a monopolar operating mode 168. In the monopolar operating mode 168, the electrosurgical medical device 100 can be used in a fifth arrangement 170, a sixth arrangement 172, and a seventh arrangement 174.

With reference to FIGS. 1 and 2b, in the fifth arrangement 170, therapeutic power is provided to the first electrode 112. More specifically, therapeutic power is provided from the therapy power supply 110 to the first electrode 112 via first electrode therapy power supply connection 130. By closing one or both of the switches 124, 128, therapeutic power can be provided to the first electrode 112 via the first therapeutic power connection 122 and/or second therapeutic power connection 126, respectively. During use, the therapeutic power can communicate from the therapy power supply 108 to the first electrode 112, through the anatomy, to the patient pad 120 and back to the therapy power supply 110 via the patient pad connection 144. In use, the functional feature 152 of the first extension 146 can contact a selected portion of the anatomy, and a device function can be performed on that portion of the anatomy. The first electrode 112 can also be optionally and/or selectively heated. That is, by supplying heating power from the heating power supply 108 to the heater 114, the first electrode 112 can be resistively heated.

In the sixth arrangement 172, therapeutic power is provided from the therapy power supply 110 to the second electrode 116 via the second electrode therapeutic power supply connection 138. The therapeutic power can communicate through the patient pad 120 to the therapeutic power supply 110 via the patient pad connection 144. Accordingly, therapeutic power flows between the second electrode 116 and the patient pad 120. In use, the functional feature 152 the second extension 148 can contact a selected portion of the anatomy, and a device function can be performed using the second electrode 116. The first electrode 112 can be optionally heated by supplying heating power from the heating power supply 108 to the heater 114.

In the seventh arrangement 174, the electrode switch 142 is closed so that therapeutic power is provided from the therapeutic power supply 110 to the third electrode 118. The therapeutic power can communicate through the patient pad 120 to the therapeutic power supply 110 via the patient pad connection 144. Accordingly, therapeutic power flows between the third electrode 118 and the patient pad 120. In use, the functional feature 152 of the third extension 150 can contact a selected portion of the anatomy, and a device function can be performed using the third electrode 118. The first electrode 112 can be optionally heated by supplying heating power from the heating power supply 108 to the heater 114.

Figure 3:
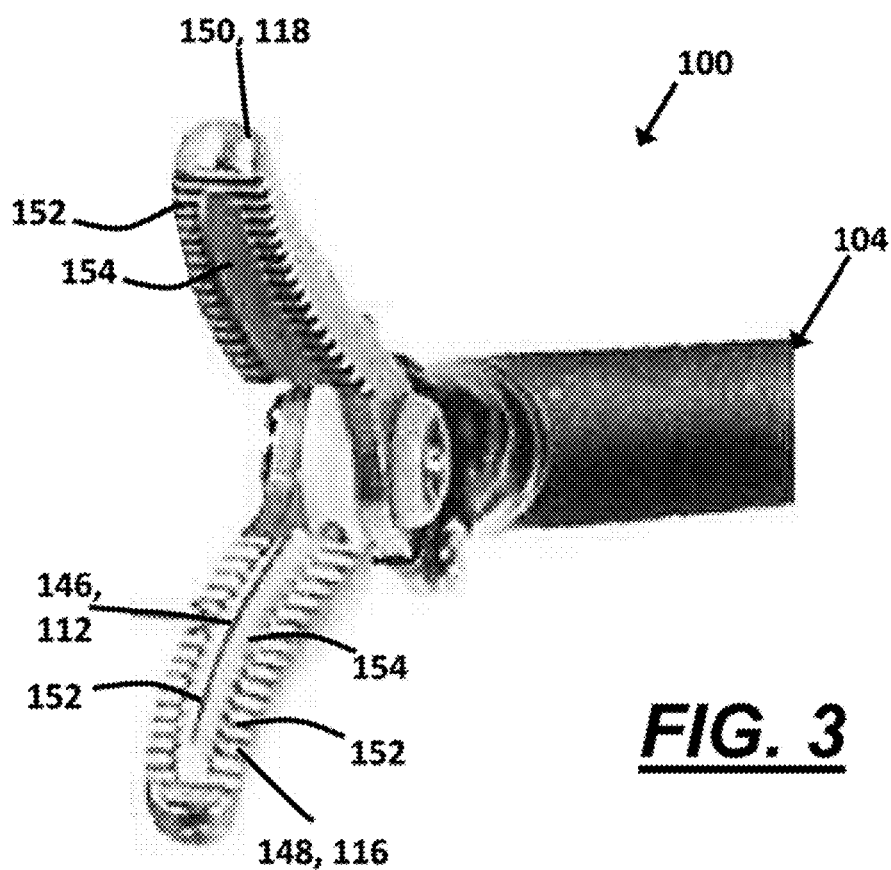
FIG. 3 illustrates a perspective view of a medical device according to the teachings herein.

FIG. 3 illustrates an exemplary electrosurgical medical device 100. The electrosurgical medical device 100 includes a hand piece 104, a first electrode 112 in communication with a first extension 146, a second electrode 116 in communication with a second extension 148, and a third electrode 118 in communication with a third extension 150. Optionally, the first electrode 112 can be in communication with the second extension 148. Optionally, the second extension 148 and the third extension 150 can be the same or connected. The second and third extensions 116, 118 include an insulating material 154 intended to restrict or prevent accidental arcing and/or heat transfer between the electrodes. Each of the extensions 146, 148, 150 includes a functional feature 152. More specifically, the function features 152 on the second and third extensions 148, 150 can be teeth, while the functional feature 152 associated with the first extension 146 can be a blade. The electrosurgical medical device 100 of FIG. 3 may be substantially similar to the medical devices shown in FIGS. 2a and 2b, except that the first extension 146 is generally stationary (e.g., is not independently moveable) relative to the second extension 148. However, the electrosurgical medical device 100 of FIG. 3 can perform in one or more of the aforementioned modes. That is, the electrodes and the extensions can be used in one or more of the arrangements described in FIGS. 2a and 2b. For example, therapeutic power can be communicated to the first electrode 112, to or through tissue, and back to the therapy power supply 110 via the patient pad 120 (not illustrated), via one or both of the second and third electrode 116, 118, or a combination thereof. Likewise, the first electrode 112 can be optionally heated. That is, by supplying heating power from the heating power supply 108 to the heater 114, the first electrode 112 can be resistively heated.

In other arrangements, therapeutic power can be supplied between the second and third electrodes 116, 118 and back to the therapy power supply 110.

FIG. 4 illustrates an exemplary electrosurgical medical device 100. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes may be in communication with one or more extensions. Optionally, two or more extensions may be the same or connected together. At least one of the extensions 146, 148, 150 includes a functional feature 152 (not illustrated). The electrosurgical medical device 100 of FIG. 4 may be substantially similar to one or more of the medical devices 100 of FIGS. 2a-3 and 5-6. In other words, the electrosurgical medical device 100 of FIG. 4 can function and perform in one or more of the aforementioned modes and configurations. For example, in one configuration, therapeutic power can be communicated to the first electrode 112, to or through tissue, and back to the therapy power supply 110 via the patient pad 120 (not illustrated), via the second electrode 116, the third electrode 118, or a combination thereof. Likewise, the first electrode 112 can be optionally heated. That is, by supplying heating power from the heating power supply 108 to the heater 114, the first electrode 112 can be resistively heated. In other configurations, therapeutic power can be supplied between the second and third electrodes 116, 118 and back to the therapy power supply 110. Moreover, the first extension 146 may or may not move in relation to the second and third extensions 148, 150, which may also move or be restricted from moving. The extensions 116, 118 of FIG. 4 also include an insulating material 152 intended to restrict or prevent arcing and/or heat transfer between the electrodes 112, 116, 118.

FIG. 5 illustrates an exemplary electrosurgical medical device 100, which may be a J Hook. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes may be in communication with one or more extensions. Optionally, two or more extensions may be the same or connected together. At least one of the extensions 146, 148, 150 includes a functional feature 152 (not illustrated). The electrosurgical medical device 100 of FIG. 5 may be substantially similar to one or more of the medical device shown and described in FIGS. 2a, 2b and 3-6. In other words, the electrosurgical medical device 100 of FIG. 4 can function and perform in one or more of the aforementioned modes and configurations. For example, therapeutic power can be communicated to the first electrode 112, to or through tissue, and back to the therapy power supply 110 via the patient pad 120 (not illustrated), one or both of the second and third electrodes 116, 118, or a combination thereof. Likewise, the first electrode 112 can be optionally heated. That is, by supplying heating power from the heating power supply 108 to the heater 114, the first electrode 112 can be resistively heated. In other configurations, therapeutic power can be supplied between the second and third electrodes 116, 118 and back to the therapy power supply 110. Moreover, the first extension may or may not move relative to the second and third extensions 148, 150.

FIG. 6 illustrates an exemplary electrosurgical medical device 100, which may be a medical spatula. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes may be in communication with one or more extensions. Optionally, two or more extensions may be the same or connected together. At least one of the extensions 146, 148, 150 includes a functional feature 152 (not illustrated). The electrosurgical medical device 100 of FIG. 6 may be substantially similar to the medical device of FIGS. 2a, 2b, and 3. In other words, the electrosurgical medical device 100 of FIG. 4 can function and perform in one or more of the aforementioned modes and configurations. For example, therapeutic power can be communicated to the first electrode 112 to or through tissue and back to the therapy power supply 110 via the patient pad 120 (not illustrated), the second electrode 116, the third electrode 118, or a combination thereof. Likewise, the first electrode 112 can be optionally heated. That is, by supplying heating power from the heating. In other configurations, therapeutic power can be supplied between the second and third electrodes 116, 118 and back to the therapy power supply 110. power supply 108 to the heater 114, the first electrode 112 can be resistively heated. Moreover, the first extension may or may not move relative to the second and third extensions 148, 150.

Figure 7:
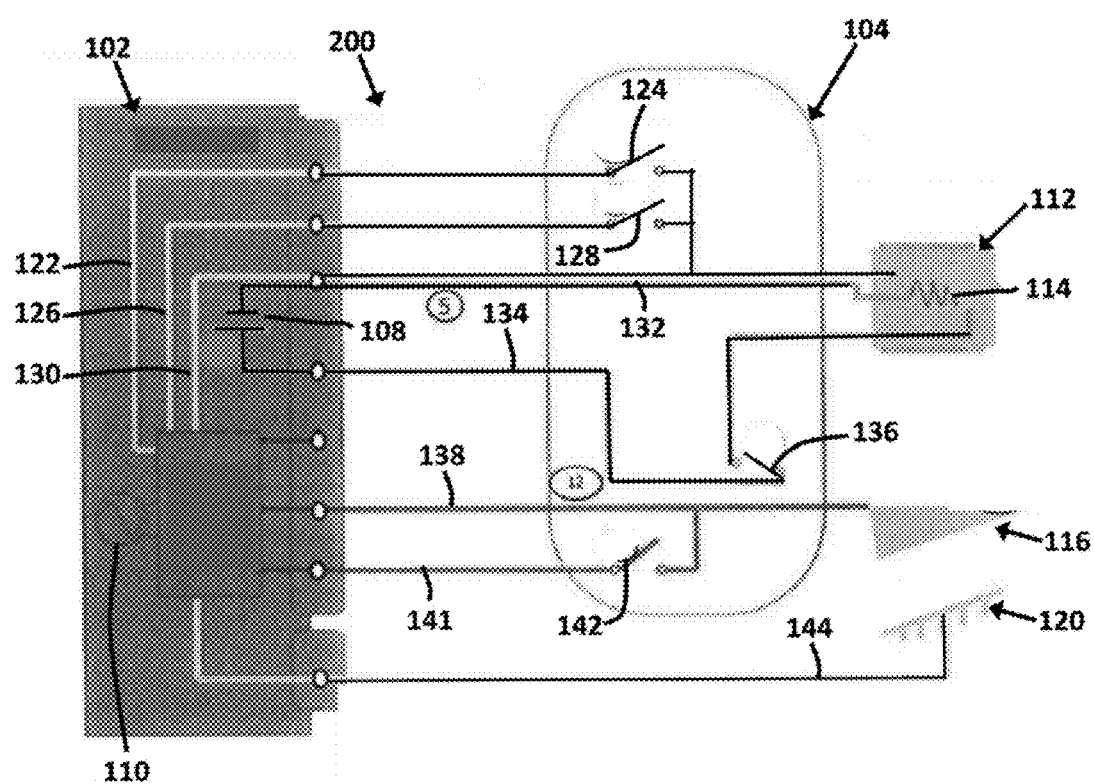
FIG. 7 illustrates a schematic of a circuit of a medical device according to the teachings herein.

FIG. 7 illustrates a schematic circuit of an electrosurgical medical device 200. The medical device 200 generally includes an electrosurgical generator 102 and a hand piece 104. The electrosurgical generator 102 includes a heating power supply 108 and a therapy power supply 110. The heating power supply 108 provides heating power to the electrosurgical medical device 200, and the therapy power supply 110 provides therapeutic power to the electrosurgical medical device 200. The electrosurgical medical device 200 includes a first electrode 112, which may comprise a heater 114, and a second electrode 116. A patient pad 120 is in electrical communication with the electrosurgical medical device 200 and the therapy power supply 110.

A first therapeutic power connection 122, which includes a first therapeutic power switch 124, extends between the therapy power supply 110 and the first electrode 112. The first therapeutic power switch 124 provides selective communication of therapeutic power between the therapy power supply 110 and the first electrode 112. A second therapeutic power connection 126, which includes a second therapeutic power switch 128, extends between the therapy power supply 110 and the first electrode 112. The second monopolar therapeutic power switch 128 provides selective communication of therapeutic power between the therapy power supply 110 and the first electrode 112. A third therapeutic power connection 130 extends between the therapy power supply 110 and the first electrode 112, which provides therapeutic power to the first electrode 112. When one or both of the first and second therapeutic power switches 124, 128 are closed, therapeutic power is provided to the first electrode 112.

A first heating power connection 132 extends between the heating power supply 108 and the heater 114 of the first electrode 112. A second heating power connection 134, which includes a heating power switch 136, extends between the heating power supply 108 and the first electrode 112. When the heating power switch 136 is closed, heating power is provided to the heater 114 to heat the first electrode 112. When the heating power switch 136 is open, heating power is restricted from communicating to the heater 114 and, as such, the first electrode 112 is not heated.

A fourth therapeutic power connection 138 extends between the therapy power supply 110 and the second electrode 116. A sixth therapeutic power connection 141, which includes an electrode switch 142, extends between the therapy power supply 110 and third electrode 118. Closing the electrode switch 142 can provide therapeutic power from the therapy power supply 110 to the second electrode 116. A patient pad connection 144 extends between the therapy power supply 110 and the patient pad 120.

In a bipolar operating mode, at least one of the switches 124, 128 are closed and therapeutic power is communicated from the therapy power supply 110 to the first electrode 112 and back to the therapy power supply 110 via the second electrode 116, (i.e., bipolar mode). Alternatively, In a monopolar operating mode, the first electrode therapeutic power circuit can be closed by communicating the therapeutic power from the therapy power supply 110 to the first electrode 112 and back to the therapy power supply 110 via a remote or patient pad 120.

Figure 8A:
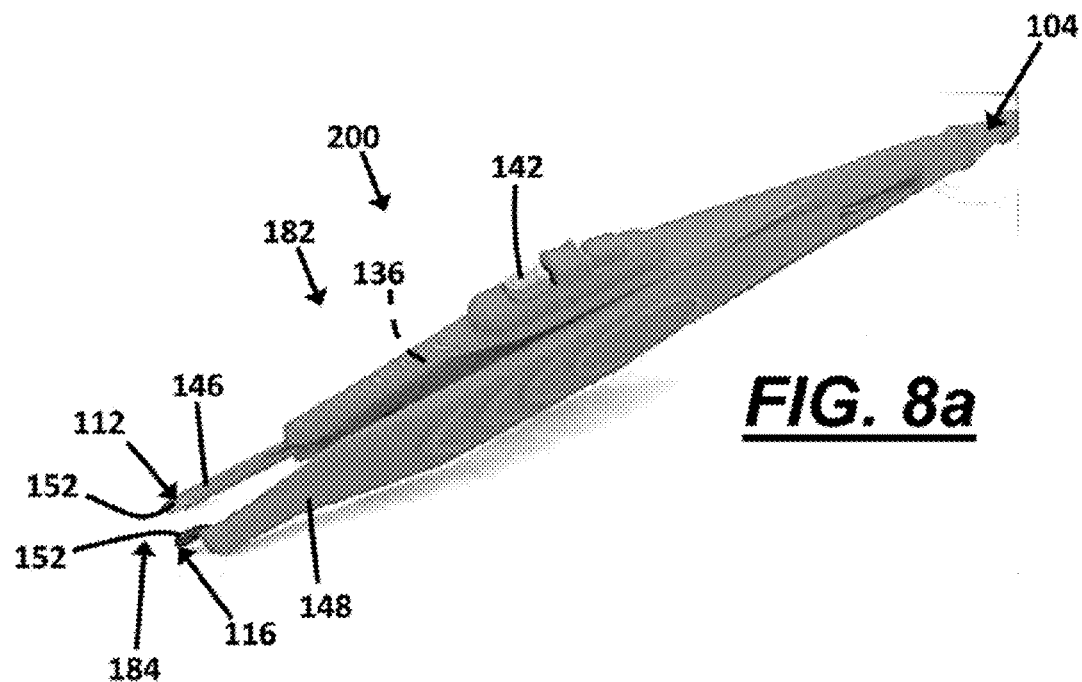
FIG. 8a illustrates a perspective view of a medical device according to the teachings herein.

FIG. 8a illustrates an exemplary electrosurgical medical device 200 in a bipolar mode 182. The medical device 200 includes a hand piece 104 comprising a first extension 146 and a second extension 148. Each extension 146, 148 includes a functional feature 152. The first electrode 112 is in communication with the first extension 146, and the second electrode 116 is in communication with the second extension 148. The first extension 146 is moveable relative to the second extension 148. In the bipolar mode 182, the medical device 200 can perform a device function in an eighth configuration 184.

With reference to FIGS. 7 and 8a, in the eighth arrangement 184, therapeutic power is provided to the first and second electrodes 112, 116. More specifically, therapeutic power is provided from the therapy power supply 110 to the first electrode 112 via the first electrode therapy power supply connection 130. The therapeutic power is provided to the second electrode 116 via the second electrode therapy power supply connection 138 and the fourth electrode therapy supply connection 141 (i.e., closing electrode switch 142). Accordingly, therapeutic power flows between the first and second electrodes 112, 116. In use, a selected portion of the anatomy can be placed between the functional features 152 of the first and second extensions 146, 148, and a device function can be performed on that portion of the anatomy. While performing a device function in the eighth configuration 184, the first electrode 112 can be optionally heated. That is, by closing the heating power switch 136 and supplying heating power from the heating power supply 108 to the heater 114, the first electrode 112 can be resistively heated.

Figure 8B:
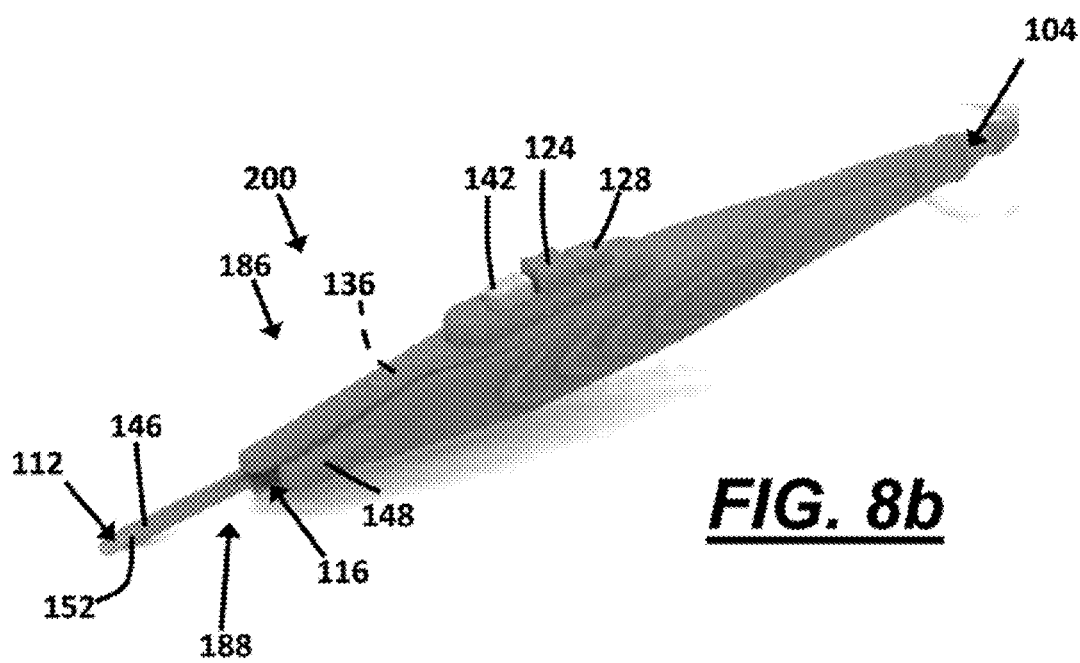
FIG. 8b illustrates a perspective view of a medical device according to the teachings herein.

FIG. 8b illustrates the electrosurgical medical device 200 in a monopolar operating mode 186. In the monopolar operating mode 186, the medical device 200 can be used in a ninth configuration 188.

With reference to FIGS. 7 and 8b, in the ninth arrangement 188, therapeutic power is provided to the first electrode 112. That is, therapeutic power is provided from the therapy power supply 110 to the first electrode 112 via first electrode therapy power supply connection 130. By closing a respective switch 124, 128, therapeutic power can be provided from the therapy power supply 110 to the first electrode 112 via the first therapeutic power connection 122 and/or second therapeutic power connection 126. The therapeutic power can communicate through the patient pad 120 to the therapy power supply 110 via the patient pad connection 144. Accordingly, therapeutic power flows between the first electrode 112 and the patient pad 120. In use, the functional feature 152 of the first extension 146 can contact a selected portion of the anatomy, and a device function can be performed. The first electrode 112 can be optionally heated. That is, by supplying heating power from the heating power supply 108 to the heater 114, the first electrode 112 can be resistively heated.

Figure 9:
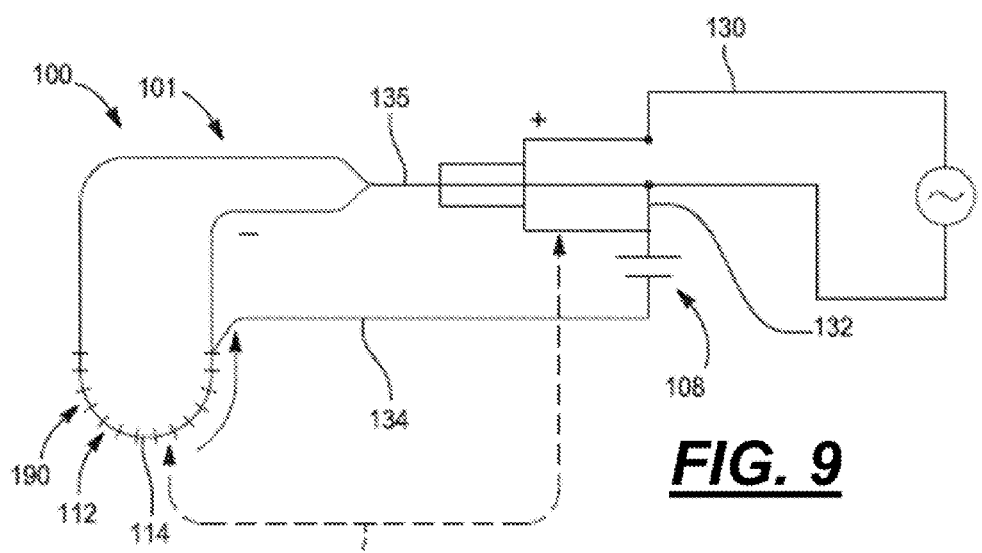
FIG. 9 illustrates an example of a circuit diagram of a resectoscope loop.

FIG. 9 illustrates a schematic circuit of an electrosurgical medical device 100 that may be a resectoscope loop electrode 101. The electrosurgical medical device 100 includes a heating power supply 108 and a therapy power supply 110. The electrosurgical medical device 100 includes a first electrode 112 that may be a loop electrode 190. The first electrode 112 includes a heater 114.

A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. An ablation path 192 extends from the first electrode 112, the heater 114, or both to the heating power connection 132.

Figure 10:
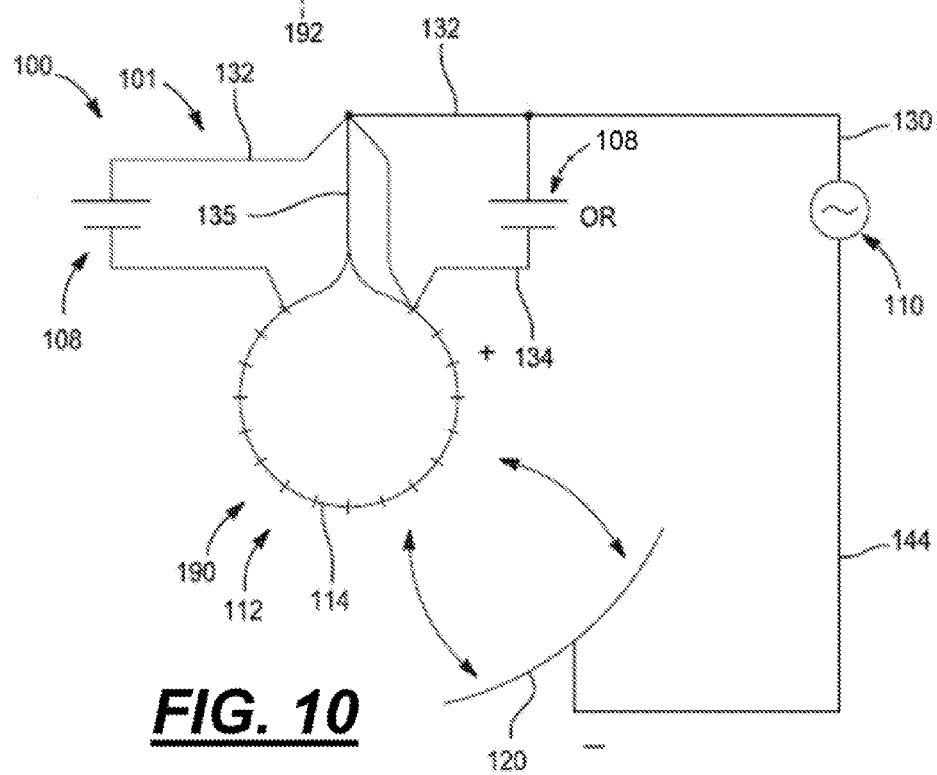
FIG. 10 illustrates a circuit diagram of one possible monopolar snare.

FIG. 10 illustrates a schematic circuit of an electrosurgical medical device 100 that may be a monopolar snare 101. The electrosurgical medical device 100 includes a heating power supply 108 and a therapy power supply 110. The heating power supply 108 can be located in one or both of the areas shown in FIG. 10. The electrosurgical medical device 100 includes a first electrode 112 that may be a loop electrode 190. The first electrode 112 includes a heater 114. A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. A patient pad connection 144 extends between the therapy power supply 110 and the remote or patient pad 120.

Figure 11A:
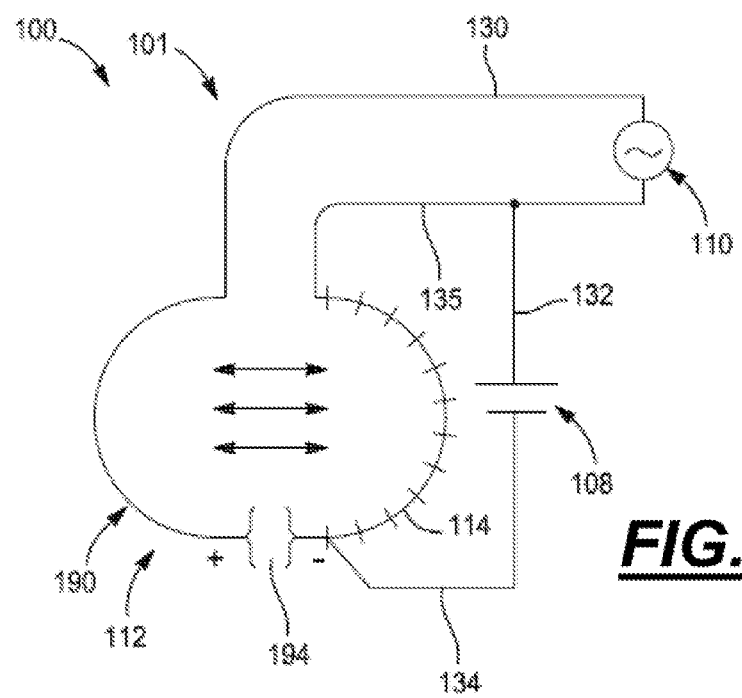
FIG. 11a illustrates a circuit diagram of one possible bipolar snare.

FIG. 11a illustrates a schematic circuit of an electrosurgical medical device 100 that may be a bipolar snare 101. The electrosurgical medical device 100 includes a heating power supply 108 and a therapy power supply 110. The electrosurgical medical device 100 includes a first electrode 112 that may be a loop electrode 190. The first electrode 112 includes a heater 114. A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. At the distal end of the electrosurgical medical device 100 is a non-conductive joint 194, so there is no necessity for a conductive break at a proximal end of the loop electrode 190.

Figure 11B:
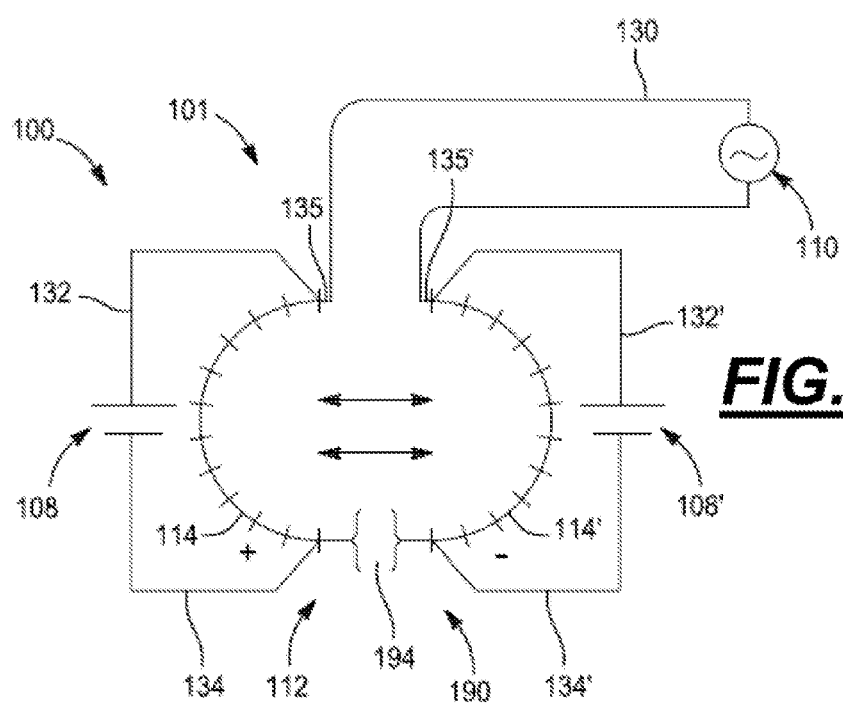
FIG. 11b illustrates a circuit diagram of one possible bipolar snare.

FIG. 11b illustrates a schematic circuit of an electrosurgical medical device 100 that may be a bipolar snare 101. The electrosurgical medical device 100 includes one or both heating power supplies 108, 108' as shown, and a therapy power supply 110. The electrosurgical medical device 100 includes a first electrode 112 that may be a loop electrode 190. The first electrode 112 includes one or both heaters 114, 114' shown that are in communication with corresponding power supplies 108, 108'. A therapeutic power connection 130 extends between the therapy power supply 110 and the first electrode 112, which provides therapeutic power to the first electrode 112. A heating power connection 132, 132' extends between the corresponding heating power supply 108, 108' and the corresponding heater 114, 114' of the first electrode 112. At the distal end of the electrosurgical medical device 100 is a non-conductive joint 194, so there is no necessity for a conductive break at a proximal end of the loop electrode 190.

The heating power connection 132 or 132' and the therapeutic power connection 130 can be a single, common connection 135 135' carrying two signals from the heating power supply 108 and the therapy power supply 110. That is, the connection 135, 135' can carry therapeutic power to the first electrode 112 and heating power to the heater 114, 114'. A second heating power connection 134, 134' extends between the heating power supply 108, 108' and the first electrode 112.

It is understood that the any one or more of the aforementioned modes and arrangements can be modified and/or combined into one or more electrosurgical configurations to perform a device function. For example, in some medical devices, it may be desirable to combine the first arrangement 162 and the fifth arrangement 170 into an electrosurgical combination to perform one or more device functions.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values, which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

We claim:

1. A medical device, comprising:
   i. a hand piece comprising a first electrode including a heater, a second electrode, and a third electrode;
   ii. a heating power supply selectively providing heating power to the heater; and
   iii. a therapy power supply selectively providing therapeutic power to the first electrode,
   wherein the medical device is changeable between operating in a first electrosurgical configuration and in a second electrosurgical configuration,
   wherein in the first electrosurgical configuration, the heating power supply provides the heating power to the heater to heat the first electrode and the therapy power supply provides the therapeutic power to the first electrode,
   wherein in the second electrosurgical configuration, the second electrode is in communication with the therapy power supply and the second electrode is also in communication with the first electrode, the third electrode, or both, and
   wherein in the second electrosurgical configuration, the medical device operates in a bipolar mode.

2. The medical device of claim 1, wherein in the first electrosurgical configuration, the first electrode is in communication with a remote electrode,
   wherein in the first electrosurgical configuration, the medical device operates in a monopolar mode.

3. The medical device of claim 2, wherein the first electrode is in communication with a first extension,
   wherein in the first electrosurgical configuration, the first extension member is a heated monopolar blade, and
   wherein the first extension member is moveable relative to any other extensions.

4. The medical device of claim 1,
   wherein in the first electrosurgical configuration, the second electrode is in communication with the therapy power supply, and
   wherein in the first electrosurgical configuration, the medical device operates in a bipolar mode.

5. The medical device of claim 4, wherein the first electrode is in communication with a first extension and the second electrode is in communication with a second extension,
   wherein in the first electrosurgical configuration, the first and second extensions comprise opposing jaws of a forceps device.

6. The medical device of claim 5, wherein the heater is electrically connected to the heating power supply by a first conductive path comprising a first connection and a second connection,
    wherein the first electrode is electrically connected to the therapy power supply by a second conductive path comprising a third connection, and
    wherein the first connection and third connection are a single, electrically connected connection providing the heating power to the heater and the therapeutic power to the first electrode.

7. The medical device of claim 1, wherein the first electrode is operable in both the first electrosurgical configuration and the second electrosurgical configuration.

8. The medical device of claim 7,
    wherein in the second electrosurgical configuration, the first electrode is in communication with the second electrode and the therapy power supply, and
    wherein in the second electrosurgical configuration, the heating power supply selectively provides heating power to the heater.

9. The medical device of claim 8,
    wherein the third electrode is in communication with at least one of the first and second electrodes in the second electrosurgical configuration.

10. The medical device of claim 4, wherein the first electrode is in communication with a first extension, the second electrode is in communication with a second extension, and the third electrode is in communication with a third extension,
    wherein in the first electrosurgical configuration, the first extension member is a heated blade, and
    wherein in the second electrosurgical configuration, the second and third extensions comprise opposing jaws of a forceps device.

11. The medical device of claim 10, wherein the medical device selectively operates in the first and second electrosurgical configurations.

12. The medical device of claim 10, wherein the heater is electrically connected to the heating power supply by a first conductive path comprising a first connection and a second connection,
    wherein the first electrode is electrically connected to the therapy power supply by a second conductive path comprising a third connector, and
    wherein the first connection and third connection are a common connection.

13. The medical device of claim 1, wherein the first electrode is in communication with a first extension, the second electrode is in communication with a second extension, and the third electrode is in communication with a third extension,
    wherein in the first electrosurgical configuration, the first extension member is a heated blade, and
    wherein in the second electrosurgical configuration, the first extension comprises a centrally-located heated extension that is sandwiched between the second and third extensions.

14. The medical device of claim 13, wherein the medical device is a J-hook or a spatula.

15. A medical device, comprising:
    i. a hand piece comprising:
        a. a first electrode including a heater,
        b. a second electrode, and
        c. a third electrode;
    ii. a heating power supply selectively supplying heating power to the heater; and
    iii. a therapy power supply selectively providing therapeutic power to the first, second, and/or third electrodes,
    wherein the medical device is selectively changeable between a first electrosurgical configuration and a second electrosurgical configuration, and
    wherein in the first electrosurgical configuration, the heating power supply provides the heating power to the heater to heat the first electrode and the therapy power supply provides the therapeutic power to the first electrode.

16. The medical device of claim 15, wherein the first electrode is in communication with a first extension, the second electrode is in communication with a second extension, and the third electrode is in communication with a third extension,
    wherein in the first electrosurgical configuration, the first extension is a heated blade,
    wherein in the second electrosurgical configuration, the therapy power supply provides the therapeutic power to the second and third electrodes so that the medical device operates in a bipolar mode, and
    wherein the second and third extensions comprise opposing jaws of a forceps device.

17. The medical device of claim 15, wherein the first electrode is in communication with a first extension, the second electrode is in communication with a second extension, and the third electrode is in communication with a third extension,
    wherein in the first electrosurgical configuration, the first extension is a heated blade,
    wherein in the second electrosurgical configuration, the therapy power supply provides the therapeutic power to the second and third electrodes so that the medical device operates in a bipolar mode, and
    wherein in the second electrosurgical mode, the second and third extensions comprise opposing segments of a medical J-hook.

18. The medical device of claim 15, wherein the first electrode is in communication with a first extension, the second electrode is in communication with a second extension, and the third electrode is in communication with a third extension,
    wherein in the first electrosurgical configuration, the first extension is a heated blade,
    wherein in the second electrosurgical mode, the therapy power supply provides the therapeutic power to the second and third electrodes so that the medical device operates in a bipolar mode, and
    wherein in the second electrosurgical configuration, the second and third extensions comprise opposing segments of a medical spatula.

19. A medical device, comprising:
    i. a hand piece comprising a first electrode including a heater;
    ii. a second electrode;
    ii. a heating power supply selectively providing heating power to heat the heater; and
    iii. a therapy power supply selectively providing therapeutic power to the first electrode, or to both of the first electrode and second electrode,
    wherein the first electrode moves relative to the second electrode.

20. A medical device, comprising:
    i. a hand piece comprising a first electrode including a heater; and ii. a heating power supply selectively providing heating power to the heater; and
iii. a therapy power supply selectively providing therapeutic power to the first electrode;
wherein the heater is electrically connected to the heating power supply by a first conductive path comprising a first connection and a second connection,
wherein the first electrode is electrically connected to the therapy power supply by a second conductive path comprising a third connection,
wherein the first connection and third connection are a common connection, and
wherein the first electrode comprises a loop electrode.

21. The medical device of claim 20, wherein the medical device comprises a second electrode, and
wherein the loop electrode is a monopolar electrode and the second electrode is a return electrode.

22. The medical device of claim 20, wherein the handpiece further comprises a second electrode, and
wherein the loop electrode and the second electrode are configured to operate in a bipolar mode.

23. The medical device of claim 22, wherein the medical device is a resectoscope or a bipolar snare.

24. The medical device of claim 21 wherein the medical device is a monopolar snare.

25. A medical device, comprising:
i. a hand piece comprising a first electrode, a second electrode, and a third electrode, the first electrode includes a heater;
ii. a heating power supply selectively providing heating power to the heater; and
iii. a therapy power supply selectively providing therapeutic power to the first electrode;
wherein the medical device is changeable between operating in a first electrosurgical configuration and in a second electrosurgical configuration;
wherein in the first electrosurgical configuration, the heating power supply is adapted to provide the heating power to the heater to heat the first electrode, and in the first electrosurgical configuration, the therapy power supply is adapted to provide the therapeutic power to the first electrode;
wherein in the second electrosurgical configuration, the first electrode is in communication with the second electrode and the therapy power supply;
wherein in the second electrosurgical configuration, the medical device operates in a bipolar mode;
wherein in the second electrosurgical configuration, the heating power supply selectively provides heating power to the heater;
wherein in the second electrosurgical configuration, the third electrode is in communication with at least one of the first and second electrodes; and
wherein the first electrode is operable in both the first electrosurgical configuration and the second electrosurgical configuration.

26. A medical device, comprising:
i. a hand piece comprising a first electrode including a heater;
ii. a heating power supply selectively providing heating power to the heater; and
iii. a therapy power supply selectively providing therapeutic power to the first electrode,
wherein the medical device is changeable between operating in a first electrosurgical configuration and in a second electrosurgical configuration;
wherein in the first electrosurgical configuration, the heating power supply is adapted to provide the heating power to the heater to heat the first electrode, and in the first electrosurgical configuration, the therapy power supply is adapted to provide the therapeutic power to the first electrode;
wherein in the first electrosurgical configuration, the first electrode is in communication with a remote electrode;
wherein in the first electrosurgical configuration, the medical device operates in a monopolar mode;
wherein the first electrode is in communication with a first extension;
wherein in the first electrosurgical configuration, the first extension member is a heated monopolar blade; and
wherein the first extension member is moveable relative to any other extensions.

27. A medical device, comprising:
i. a hand piece comprising a first electrode including a heater, and a second electrode;
ii. a heating power supply selectively providing heating power to the heater; and
iii. a therapy power supply selectively providing therapeutic power to the first electrode,
wherein the medical device is changeable between operating in a first electrosurgical configuration and in a second electrosurgical configuration;
wherein in the first electrosurgical configuration, the heating power supply is adapted to provide the heating power to the heater to heat the first electrode, and in the first electrosurgical configuration, the therapy power supply is adapted to provide the therapeutic power to the first electrode;
wherein in the first electrosurgical configuration, the medical device operates in a bipolar mode;
wherein in the first electrosurgical configuration, the second electrode is in communication with the therapy power supply;
wherein the first electrode is in communication with a first extension and the second electrode is in communication with a second extension;
wherein in the first electrosurgical configuration, the first and second extensions comprise opposing jaws of a forceps device;
wherein the heater is electrically connected to the heating power supply by a first conductive path comprising a first connection and a second connection;
wherein the first electrode is electrically connected to the therapy power supply by a second conductive path comprising a third connection; and
wherein the first connection and third connection are a single, electrically connected connection providing the heating power to the heater and the therapeutic power to the first electrode.

* * * * *